(12) United States Patent
Ernest et al.

(10) Patent No.: US 10,645,787 B2
(45) Date of Patent: May 5, 2020

(54) SYSTEM AND METHOD FOR PROVIDING ELECTRICAL POWER TO A LOAD

(71) Applicant: GENERAL ELECTRIC COMPANY, Schenectady, NY (US)

(72) Inventors: Philippe Ernest, Buc (FR); Niranjan Kumar, Bangalore (IN); Nicolas Levilly, Buc (FR); Yash Veer Singh, Niskayuna, NY (US); Guillermo Garcia Soto, Buc (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/840,325

(22) Filed: Dec. 13, 2017

(65) Prior Publication Data

US 2019/0182944 A1    Jun. 13, 2019

(51) Int. Cl.
*H02M 7/5387* (2007.01)
*H05G 1/14* (2006.01)
*A61B 6/00* (2006.01)
*H05G 1/10* (2006.01)
*H02M 7/493* (2007.01)
*H02M 1/00* (2006.01)
*H02M 7/48* (2007.01)

(52) U.S. Cl.
CPC ............. *H05G 1/14* (2013.01); *A61B 6/56* (2013.01); *H02M 7/53871* (2013.01); *H05G 1/10* (2013.01); *H02M 7/493* (2013.01); *H02M 2001/0077* (2013.01); *H02M 2007/4815* (2013.01)

(58) Field of Classification Search
CPC ............... H02M 3/1584; H02M 3/285; H02M 3/33561; H02M 7/42; H02M 7/493; H02M 7/53871; H02M 7/06; H02M 7/153; H02M 2007/4811; H02M 2007/4815; H02M 2007/4822; H02M 2007/4826; H02M 7/5387
See application file for complete search history.

(56) References Cited

U.S. PATENT DOCUMENTS

| 4,805,081 | A | * | 2/1989 | Chambers | ........... H02M 3/3155 363/136 |
| 6,528,770 | B1 | * | 3/2003 | Akel | ........................ H05B 6/04 219/624 |
| 9,263,950 | B2 | | 2/2016 | Qahouq et al. | |
| 2011/0002445 | A1 | | 1/2011 | Hattrup et al. | |
| 2012/0153995 | A1 | | 6/2012 | Oughton, Jr. | |
| 2014/0085953 | A1 | | 3/2014 | Mao | |

(Continued)

FOREIGN PATENT DOCUMENTS

CN    106100346 A    11/2016

OTHER PUBLICATIONS

Extended European Search Report from related EP Patent Application No. 18210090.9, dated May 17, 2019.

*Primary Examiner* — Adolf D Berhane

(57) ABSTRACT

A system for providing electrical power to a load is provided. The system includes at least two inverters and at least two resonant circuits. The inverters are operative to electrically connect to a power source. The resonant circuits are each electrically connected to at least one of the inverters and operative to provide electrical power to the load. The resonant circuits are coupled to each other.

17 Claims, 6 Drawing Sheets

(56) References Cited

U.S. PATENT DOCUMENTS

| | | | |
|---|---|---|---|
| 2015/0289321 A1* | 10/2015 | Uchida | H05B 6/06 219/662 |
| 2016/0164476 A1 | 6/2016 | Wang et al. | |
| 2017/0085189 A1 | 3/2017 | Madsen | |
| 2017/0098961 A1* | 4/2017 | Harpham | H02J 50/12 |
| 2017/0222488 A1* | 8/2017 | Madawala | H01F 38/14 |
| 2019/0369182 A1* | 12/2019 | Singh | G01R 33/543 |

* cited by examiner

SYSTEM AND METHOD FOR PROVIDING ELECTRICAL POWER TO A LOAD

BACKGROUND

Technical Field

Embodiments of the invention relate generally to medical imaging systems, and more specifically, to a system and method for providing electrical power to a load.

Discussion of Art

Many medical imaging systems utilize vacuum tubes to generate images of an object. Such vacuum tubes, commonly referred to as "x-ray" tubes, generally include a cathode disposed at a distance from an anode within a vacuum vessel. The anode usually includes an impact zone that is generally fabricated from a refractory metal with a high atomic number, such as tungsten or a tungsten alloy. A voltage difference is maintained between the cathode and the anode such that an electron beam is generated by the cathode and strikes the anode within the impact zone, typically called the focal spot. As electrons within the electron beam impact the anode, their kinetic energy is converted to high-energy electromagnetic radiation, e.g., x-rays.

Generally, the intensity and/or frequency of the electromagnetic radiation generated by a vacuum tube is determined, in part, by the magnitude of the voltage differential between the cathode and the anode. Accordingly, many such medical imaging systems utilize power converters/conditioners to control/regulate the type and/or amount of electrical power supplied to the anode and/or cathode, i.e., the load. Many such power converters/conditioners, however, typically include specially designed inverters arranged in a circuit customized to a particular application. Designing such customized circuits, however, is usually an expensive and/or time consuming process. Moreover, increasing the number of inverters in such customized circuits often requires including numerous hardware components to facilitate control over the additional inverters.

What is needed, therefore, is an improved system and method for providing electrical power to a load.

BRIEF DESCRIPTION

In an embodiment, a system for providing electrical power to a load is provided. The system includes at least two inverters and at least two resonant circuits. The inverters are operative to electrically connect to a power source. The resonant circuits are each electrically connected to at least one of the inverters and operative to provide electrical power to the load. The resonant circuits are coupled to each other.

In another embodiment, a method of providing electrical power to a load is provided. The method includes providing electrical power to the load via one or more resonant circuits each electrically connected to at least one of two inverters electrically connected to a power source. The resonant circuits are coupled to each other.

In yet another embodiment, a non-transitory computer readable medium storing instructions is provided. The instructions are configured to adapt a controller to vary electrical power provided to a load by two resonant circuits that are each connected to at least one of two inverters electrically connected to a power source. The resonant circuits are coupled to each other.

DRAWINGS

The present invention will be better understood from reading the following description of non-limiting embodiments, with reference to the attached drawings, wherein below:

DETAILED DESCRIPTION

Figure 1:
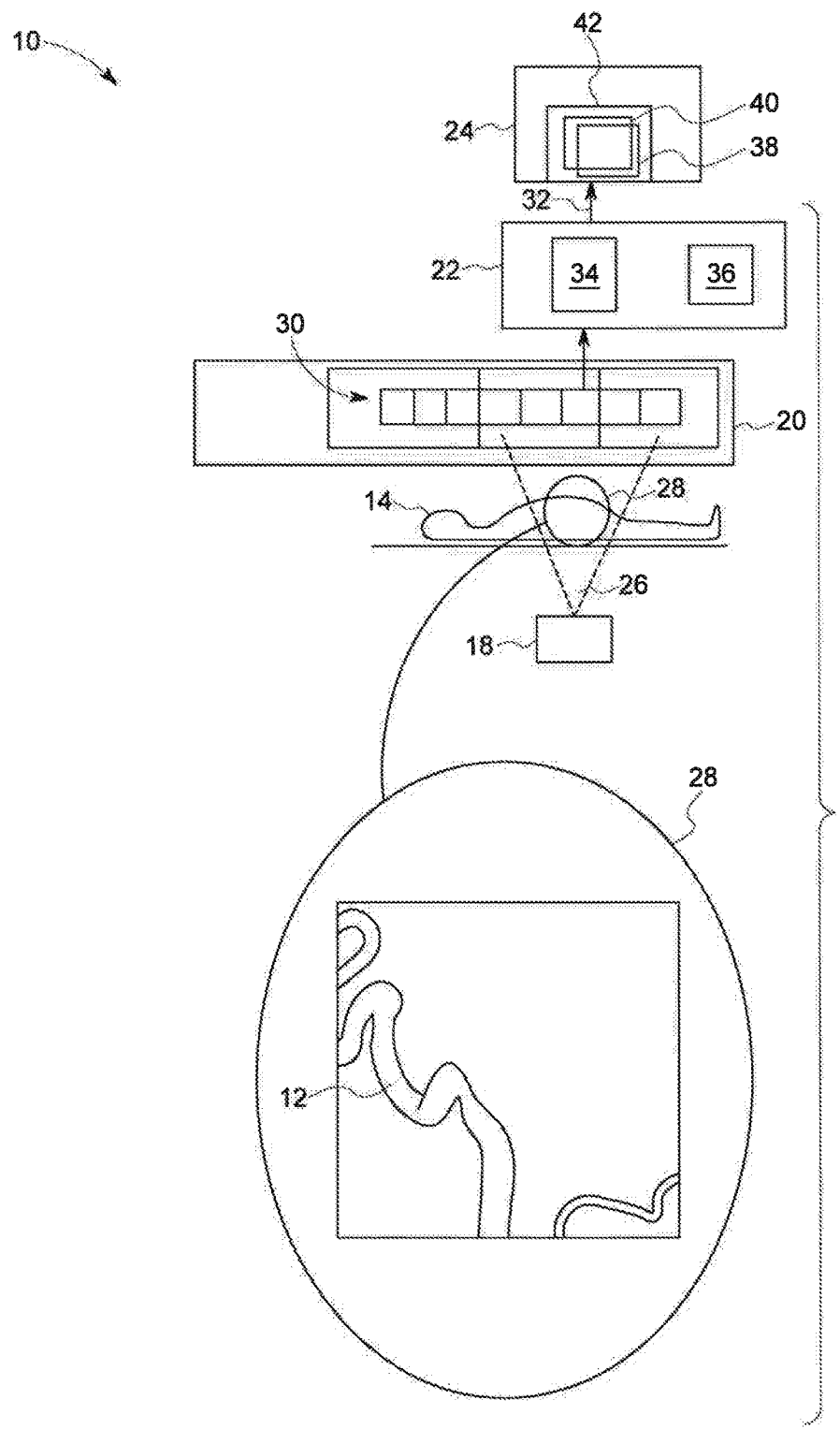
FIG. 1 is a block diagram of an imaging system having a system for providing electrical power to a load, in accordance with an embodiment of the present invention.

Reference will be made below in detail to exemplary embodiments of the invention, examples of which are illustrated in the accompanying drawings. Wherever possible, the same reference characters used throughout the drawings refer to the same or like parts, without duplicative description.

As used herein, the terms "substantially," "generally," and "about" indicate conditions within reasonably achievable manufacturing and assembly tolerances, relative to ideal desired conditions suitable for achieving the functional purpose of a component or assembly. As used herein, "electrically connected," and "electrical communication" mean that the referenced elements are directly or indirectly connected such that an electrical current may flow from one to the other. The connection may include a direct conductive connection, i.e., without an intervening capacitive, inductive or active element, an inductive connection, a capacitive connection, and/or any other suitable electrical connection. Intervening components may be present. The term "coupled", as used herein with respect to two elements, means that energy may electromagnetically transfer between the two elements, e.g., the transfer of electrical energy from one circuit to another circuit. The term "real-time," as used herein, means a level of processing responsiveness that a user senses as sufficiently immediate or that enables the processor to keep up with an external process. As further used herein, the terms "imaging procedure" and/or "medical imaging procedure" refer to a medical procedure that involves an imaging system to assist in accomplishing one or more tasks. Accordingly, as also used herein, the term "task" means an objective of a medical procedure, e.g., obtaining a biopsy, deploying/installing a stent into a blood vessel, locating an ulcer, imaging a clogged artery, suturing a patient, and/or other medical processes.

Additionally, while the embodiments disclosed herein are described with respect to an x-ray based imaging system, it is to be understood that embodiments of the present invention are equally applicable to other devices that utilize electrical power supplies and/or electrical power converters. As will be appreciated, embodiments of the present invention related imaging systems may be used to analyze objects within any material which can be internally imaged, generally. As such, embodiments of the present invention are not limited to analyzing objects within human tissue.

Referring now to FIG. 1, a medical imaging system 10 in accordance with an embodiment of the present invention is shown. As will be understood, the system 10 is operative to image a structure 12, e.g., an internal organ, blood vessel, etc., within a the subject/patient 14. For example, the patient 14 may be undergoing a stent implant medical procedure, and the imaged structure 12 may be a coronary artery. As shown in FIG. 1, the imaging system 10 includes: a radiation source 18 and a radiation detector 20, which collectively form an imaging device; a controller 22; and a display screen 24. The radiation source 18 projects a radiation beam 26 through a region of interest ("ROI") 28 of the patient 14 within which the structure 12 is disposed. The radiation beam 26 is received by the radiation detector 20, which generates a plurality of images 30 that are then communicated to the controller 22, which generates a video feed 32 that is transmitted to and displayed by the display screen 24. As will be appreciated, in embodiments, the radiation detector 20 and/or radiation source 18 may be mobile units, e.g., part of a mobile x-ray system for imaging a patient 14 while minimizing movement 14 of the patient. The radiation beam 26 may include various types of electromagnetic radiation, to include ionizing electromagnetic radiation such as x-rays and/or gamma rays.

As further shown in FIG. 1, the controller 22 includes at least one processor/CPU 34 and at least one memory device 36, and is in electronic communication with the radiation source 18, detector 20, and/or the display screen 24. An imaging program/application may be stored in the at least one memory device 36 that, when loaded into the at least one processor 34, adapts the controller 22 to generate the video feed 32 by processing the images 30 received from the detector 20. In embodiments, the imaging program may further adapt the controller 22 to control the detector 20 and/or the radiation source 18.

The video feed 32 includes a plurality of frames 38, 40, and 42. As used herein, the term frame describes a composite image that may be based at least in part on one or more of the plurality of images 30 acquired by the imaging system 10. For instance, in embodiments, a single composite image/frame 42 may be generated by registering one or more of the acquired images 30 to a reference image selected from the plurality of images 30. The registration of one or more images 30 to a reference image may increase the contrast of the structure 12 within the produced/generated frame 42. Accordingly, in embodiments, each frame 38, 40, and 42 may be based at least in part on one or more of the images 30 received by the controller 22 from the detector 20. Once a frame 42 has been generated, it is transmitted, as part of the video feed 32, by the controller 22 to the display screen 24. In other words, in embodiments, the displayed video feed 32 is a processed form of the raw images 30 acquired by the imaging system 10. In embodiments, the video feed 32 may be a live/real-time and/or near-real-time feed. In other embodiments, one or more of the frames 38, 40, and 42 may be still images, e.g., a photograph.

Figure 2:
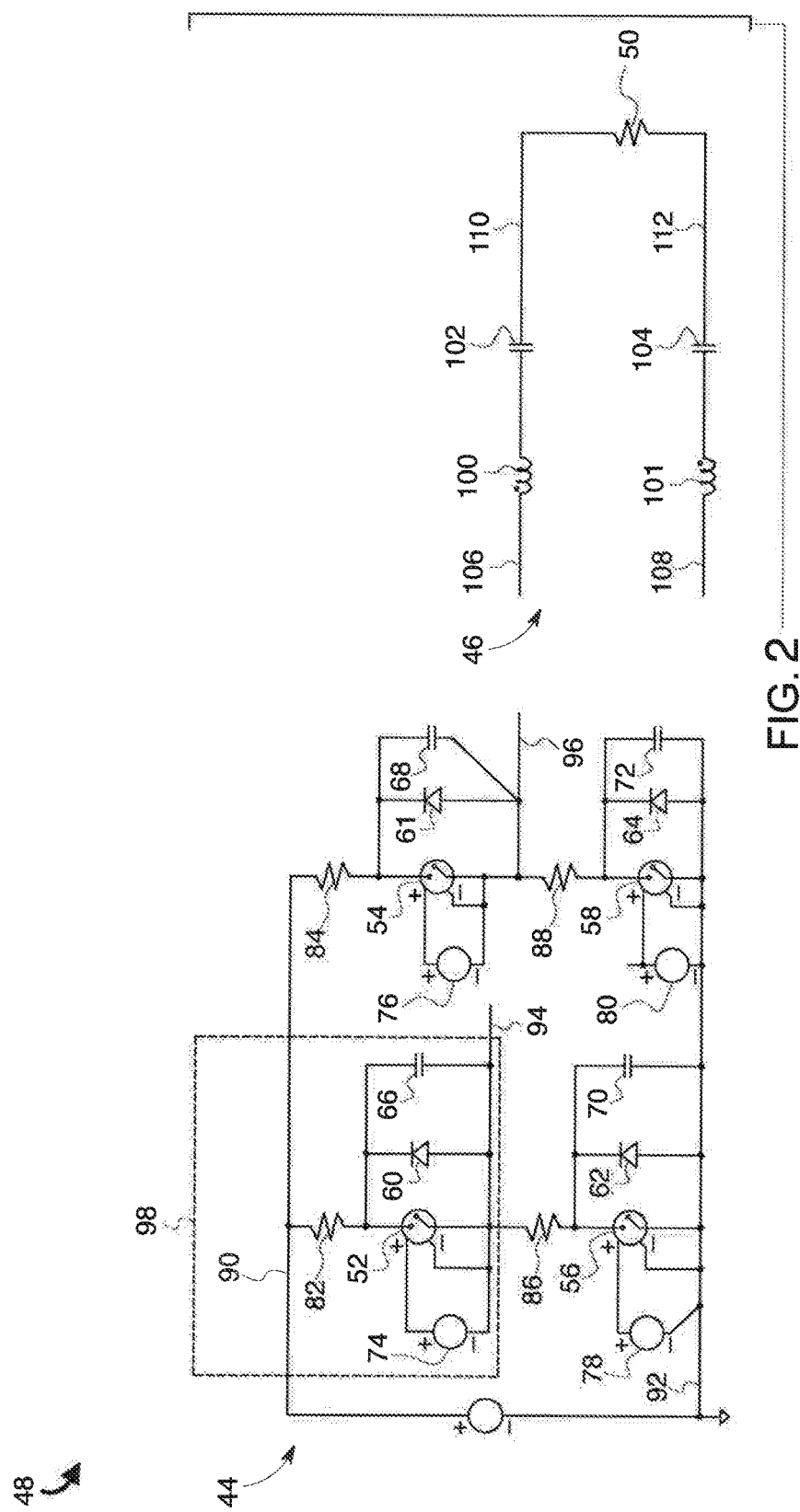
FIG. 2 is a diagram of an inverter and a resonant circuit of the system for providing electrical power to a load of the imaging system of FIG. 1, in accordance with an embodiment of the present invention.

Turning now to FIG. 2, a representative brick/module having an inverter 44 and resonant circuit 46 of a system 48 for providing electrical power to a load 50 are shown. As used herein, the terms "brick" and/or "module" refers to an inverter 44 and corresponding resonant circuit 46. While FIG. 2 depicts a single brick 44, 46, as will be explained in greater detail below, embodiments of the system 48 may include two (2) or more bricks. As shown in FIG. 2, each inverter 44 may include one or more switches 52, 54, 56, 58, e.g., MOSFETS or IGBTs, one or more antiparallel diodes 60, 61, 62, 64, e.g., the internal body diode of one or more MOSFETS, and one or more capacitors 66, 68, 70, 72. For example, the inverters 44 may be full-bridged, e.g., having four switches 52, 54, 56, 58 controlled by one or more control lines/signals 74, 76, 78, 80, and having one or more resisters 82, 84, 86, 88. While the embodiment in FIG. 2 depicts the capacitors 66, 68, 70, 72 as snubbers used in ZVS converters, other kinds of topologies and/or snubbers may be used.

Each inverter 44 may further include one or more input leads 90, 92 and one or more output leads 94, 96. The switches 52, 54, 56, 58, antiparallel diodes 60, 61, 62, 64, capacitors 66, 68, 70, 72, and resisters 82, 84, 86, 88 may be arranged/grouped into one or more power conducting devices 98, e.g., a grouping of one switch 52, antiparallel diode 60, capacitor 66, and resistor 82. Thus, in embodiments, adjusting, e.g., activating/deactivating, the switches 52, 54, 56, 58, alters/controls/sets the voltage between the output leads 94 and 96.

Some embodiments of the system 48 may not include resisters 82, 84, 86, 88, which are depicted herein as a practical way to: create unbalance between inverter arms by changing values; and to demonstrate that, thanks to the coupled inductors (as explained below), the currents and power sharing between associated inverters may not be affected. As will be appreciated, it is often difficult to associate resonant converters in serial or parallel with balanced current and power sharing due to the resonance Q factor. While traditional approaches attempt to balance through inverter control, such traditional approaches, however, usually induce control complexity, extra hardware, and/or prevent modularity. As will be appreciated, the coupling of inductors promotes/helps to ensure the proper current/power sharing, e.g., all inverter commands may be common.

As further shown in FIG. 2, each resonant circuit 46 may include one or more inductors 100, 101, e.g., inductive coils, one or more capacitors 102, 104, one or more input leads 106, 108, and one or more output leads 110, 112.

Figure 3:
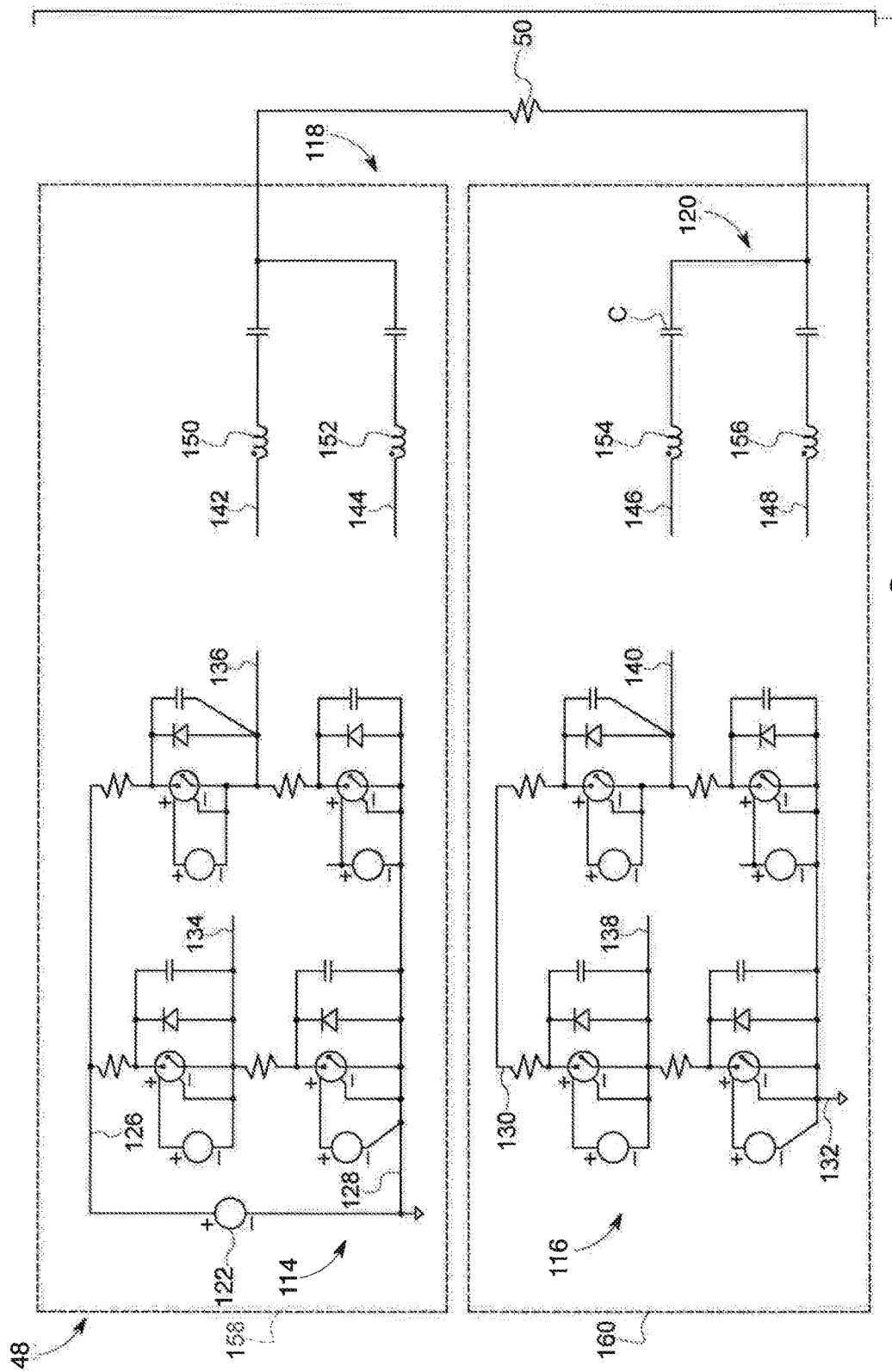
FIG. 3 is a diagram of the system for providing electrical power to a load of the imaging system of FIG. 1, in accordance with an embodiment of the present invention.

Moving to FIG. 3, the system 48 for providing electrical power to a load 50 is shown as having two bricks/modules, i.e., the system 48 may include at least two or more inverters 114, 116, and at least two or more resonant circuits 118, 120. The inverters 114, 116 are operative to electrically connect to a power source 122, e.g., a voltage source, and the resonant circuits 118, 120 are operative to provide electrical power to the load 50. As will be explained in greater detail bellow, the resonant circuits 118, 120 are coupled to each other. Further, while the load 50 is depicted herein as an equivalent load, e.g., a resistor, it will be understood that, in embodiments, the load 50 may be the radiation source 18 (FIG. 1), e.g., the system 48 may serve as the primary side of a transformer which may have a low voltage but a high current, whereas the secondary side of the transformer has a high voltage and a low current.

As further shown in FIG. 3, in embodiments, the input leads 126, 128, 130, 132 of each inverter 114, 116 may be operative to connect to the power source 122, and the output leads 134, 136, 138, 140 of each inverter 114, 116 may connect to the input leads 142, 144, 146, 148 of the resonant circuits 118, 120, i.e., the bricks may be connected to the power source 122 in parallel. For example, in embodiments, the inverters 114 and 116 may be connected to the resonant circuits 118 and 120, as follows: output lead 134 to input lead 142; output lead 136 to input lead 148; output lead 138 to input lead 146; and output lead 140 to input lead 144. In other embodiments, the inverters 114 and 116 may be connected to the resonant circuits 118 and 120 as follows: output lead 134 to input lead 142; output lead 136 to input lead 146; output lead 138 to input lead 144; and output lead 140 to input lead 148. Thus, in embodiments, each inverter 114, 116 may be electronically connected to two of the resonant circuits 118, 120. As will be appreciated, however, in embodiments having a single brick, i.e., a single inverter 44 (FIG. 2) and a single resonant circuit 46 (FIG. 2), lead 94 (FIG. 2) may be connected to lead 106 (FIG. 2) and lead 96 (FIG. 2) may be connected to lead 108 (FIG. 2).

As stated above the resonant circuits 118 and 120 may be coupled to each other. As will be appreciated, some embodiments of the present invention replace the L inductance of traditional resonant inverters with a mutual inductance, thus, adding an AC current parallelization role to the inverters 114, 116. For example, in embodiments, inductors may form the following couplings: $k_1$=inductors 150 and 152; and $k_2$=inductors 154 and 156. In such embodiments, $k_1$ and $k_2$ may each be between about 0.95 to about 1.0, e.g., about 0.99. As will be appreciated, the near 1.0 coupling coefficients ("k") enables differential current, e.g., power, to flow, due to a very low inductance of L*(1−k) and a common mode current, e.g., noise having low and/or no power, that sees L*(1+k) and is blocked. As will be further appreciated, L*(1+k) is a low value and serves as the resonant choke. L*(1−k) may be around 2*L, and may serve to block any dissymmetry of the current. In certain aspects, the whole inductance, as opposed to part of the inductance, may be used in this way, such that 2*L is large and with the dissymmetry blocking capability being efficient. Thus, there may be no need for additional controlling hardware.

Accordingly, the inverters and the bricks/modules 158 and 160 formed by the resonant circuits may be stackable/chainable such that the maximum electrical power provided to the load 50 corresponds, at least in part, on the number of modules 158 and 160 within the system 48, and where the instantaneous/current/actual electrical power provided to the load 50 is variable by adjusting the inverters 114, 116 via the switches 52, 54, 56, 58 (FIG. 2) of the power conducting devices 98 (FIG. 2), as discussed above. In embodiments, the inverters 114, 116 and/or the resonant circuits 118, 120 may be connected to each other, with respect to the load 50, in parallel, as shown in FIG. 3, or in series, as shown in FIG. 4 by the addition of a second power source 161.

The power sources 122 and/or 161 may have mains on the order of about 380-480 VAC three phase which may be rectified to about 450-750 VDC, which in turn, may be filtered by two capacitors in serial, each carrying about 225-375 VDC. Each inverter, in a serial arrangement, may have 600V switches, which may provide for improved performance over 1200V switches, which may be used in embodiments having a single inverter. In embodiments having two (2) inverters, each inverter may supply equal output current and/or the same output voltage, when connected in parallel on the output side, such that they may supply the same power. Consequently, the inverters in such embodiment may take the same input power from capacitors and/or voltage sources 122 and/or 161. As will be understood, some embodiments may have a low power active balancing circuit with voltages 122 and 161 equal in a robust way.

Figure 4:
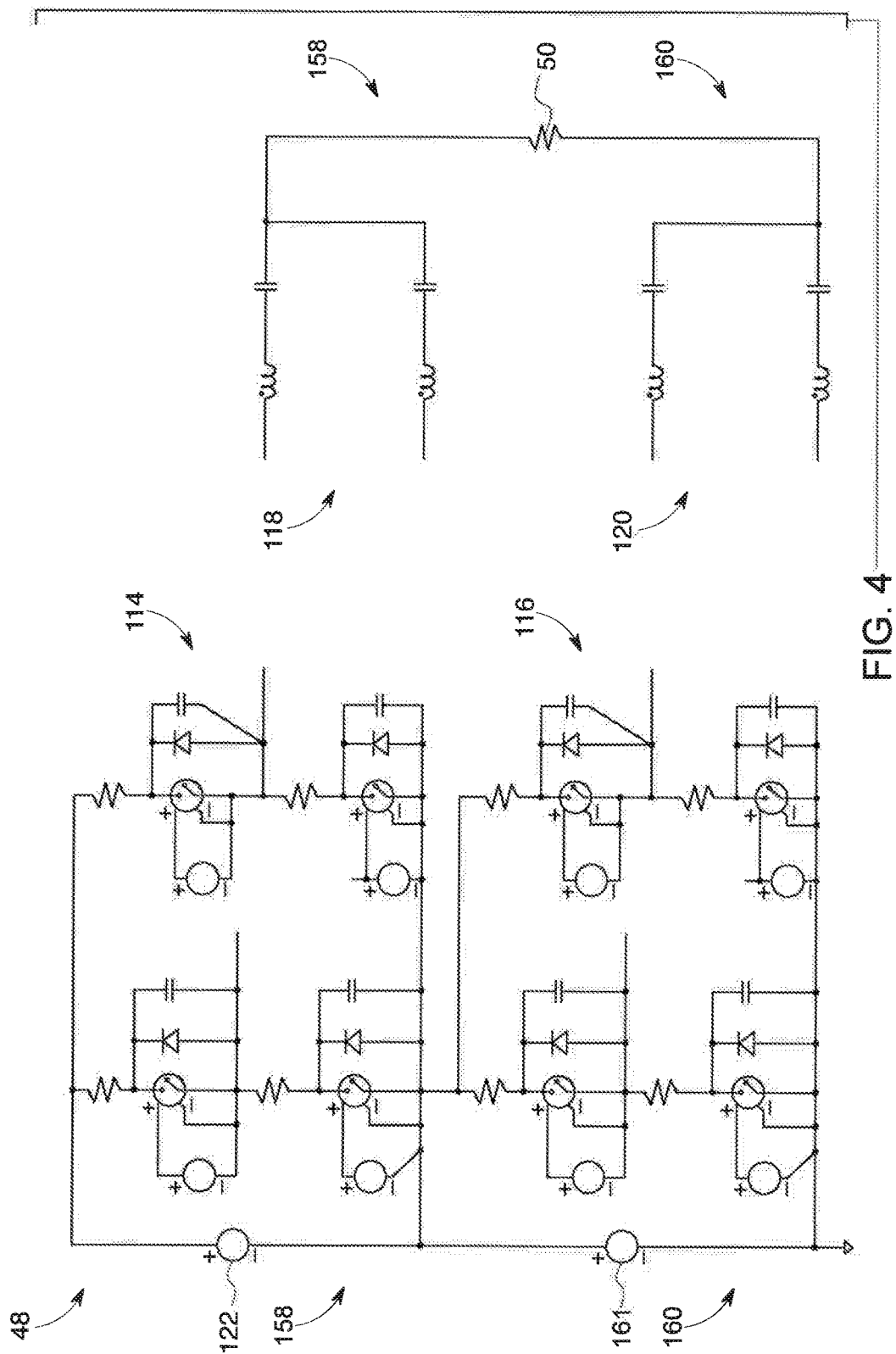
FIG. 4 is a diagram of an alternate arrangement of the system for providing electrical power to a load of FIG. 3, in accordance with an embodiment of the present invention.

While the embodiments in FIGS. 3 and 4 depict the system 48 as having two modules 158, 160, it is to be understood that the number of modules may be increased, with the additional modules being incorporated into the system 48 via substantially the same wiring/connections/pattern/circuitry, i.e., the modules 158, 160 are identical, or substantially identical, and chainable.

Figure 5:
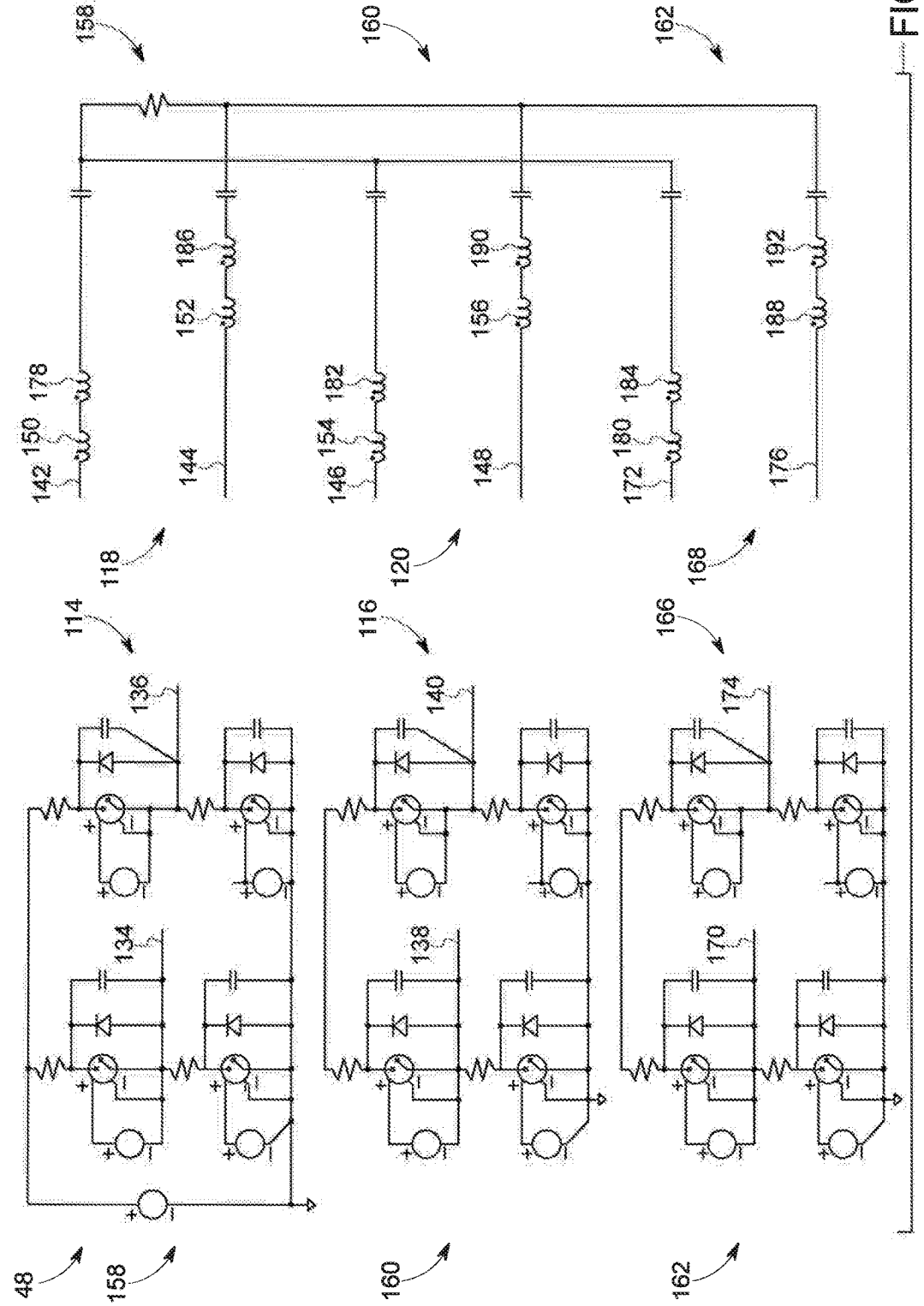
FIG. 5 is a diagram of another alternate arrangement of the system for providing electrical power to a load of FIG. 3, in accordance with an embodiment of the present invention.

For example, as illustrated in FIG. 5, the system 48 may include three or more modules 158, 160, and 162 in which the inverters 114, 116, and 166 may be connected to the resonant circuits 118, 120, and 168 as follows: output lead 134 to input lead 142; output lead 136 to input lead 144; output lead 138 to input lead 146; output lead 140 to input lead 148; output lead 170 to input lead 172; and output lead 174 to input lead 176. As will be appreciated, the resonant circuits 118, 120, and 168 in such embodiments may include additional couplings, e.g., two-by-two. For example, as shown in FIG. 5, the inductors of such embodiments may form the following couplings: $k_1$=inductors 150 and 154; $k_2$=inductors 178 and 180; $k_3$=inductors 182 and 184; $k_4$=inductors 152 and 156; $k_5$=inductors 186 and 188; and $k_6$=inductors 190 and 192.

Figure 6:
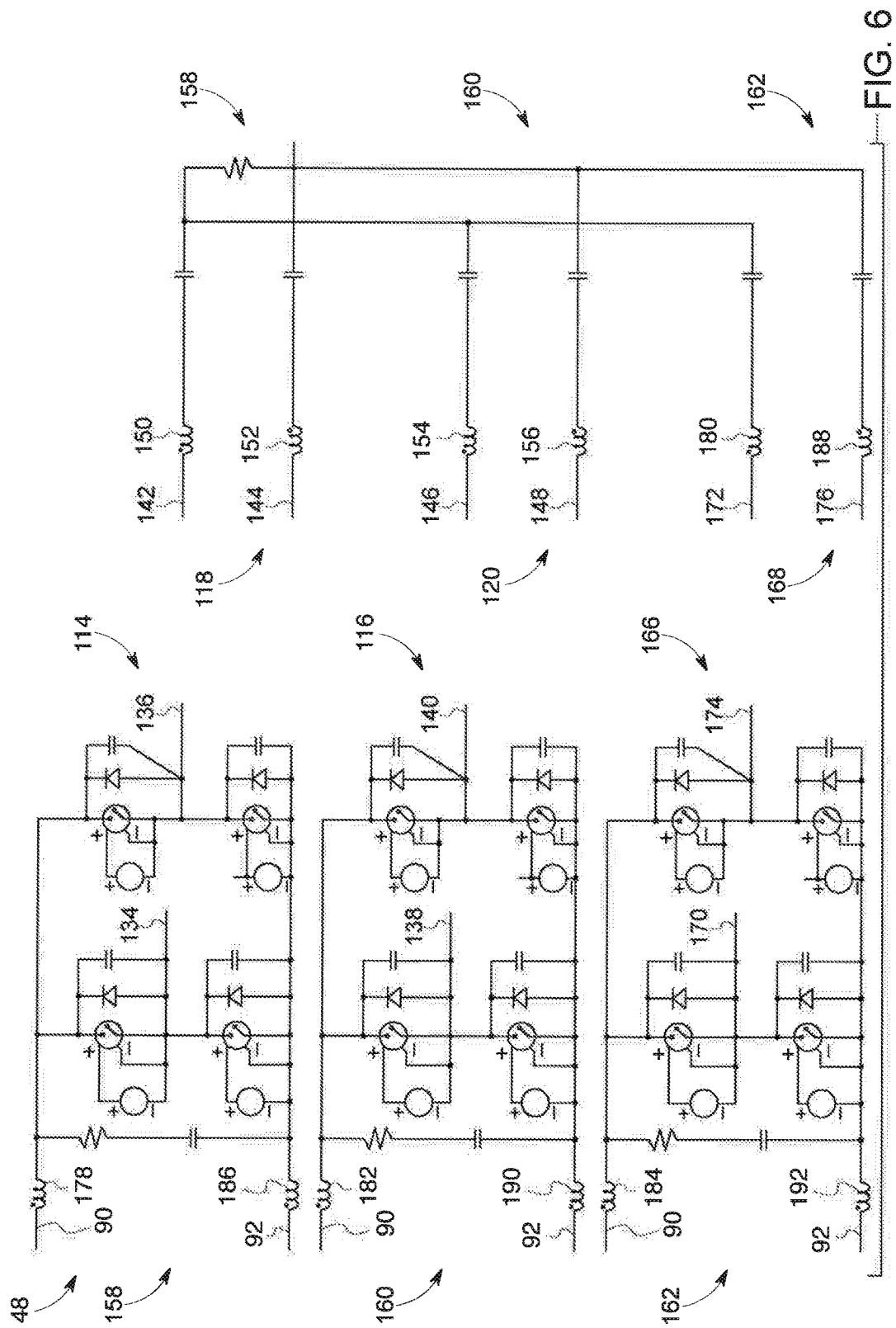
FIG. 6, is a diagram of yet another alternate arrangement of the system for providing electrical power to a load of FIG. 3, in accordance with an embodiment of the present invention.

Turning now to FIG. 6, in embodiments, the system 48 may include three or more modules 158, 160, and 162 in which the inductors may be split/divided between the resonant circuits 118, 120, 168 and the inverters 114, 116, 166, as opposed to a two-by-two arrangement (shown in FIG. 5). In other words, some of the inductors 178, 186, 182, 190, 184, 192 may be disposed in the input leads 90, 92 of the inverters 114, 116, 166, and some of the inductors 150, 152, 154, 156, 180, 188 may be disposed in the resonant circuits 118, 120, and 168. In such embodiments, the inverters 114, 116, and 166 may be connected to the resonant circuits 118, 120, and 168 as follows: output lead 134 to input lead 142; output lead 136 to input lead 176; output lead 138 to input lead 146; output lead 140 to input lead 144; output lead 170 to input lead 172; and output lead 174 to input lead 148. The inductors of such embodiments may form the following couplings: $k_1$=inductors 150 and 152; $k_2$=inductors 154 and 156; $k_3$=inductors 180 and 188; $k_4$=inductors 178 and 186; $k_5$=inductors 182 and 190; and $k_6$=inductors 184 and 192.

Thus, in such embodiments, each coupled inductance may be wired A(n) to A for a first winding, and a B(n+1) to B for a second winding, where A and B are the two (2) polarities of the load, and where A(n) and B(n) are the two (2) polarities of a particular inverter n. As will be understood, such a wiring scheme constitutes a circular permutation that may be extended without limitation to parallelize large numbers of modules. As such, calling Ian the current in the An wire, and Ibn the current in the Bn wire, some embodiments may achieve Ian=Ibn=iload/n, where the coupled inductances ensure Ia1=Ib2, Ia2=Ib3, Ia3=Ib1 and the load kirchoff law ensures Ia=Ia1+Ia2+Ia3=Ib1+Ib2+Ib3. As the system 48 does not ensure Ia1=Ia2=Ia3=Ib1=Ib2=Ib3, additional coupling may be necessary, e.g., on the DC side and not affecting the AC side so as to avoid impacting the frequency of the provided power.

As will be further appreciated, in embodiments, there may be a need to place one Cres on the output leads of the modules, e.g., the outputs of the resonant circuits, due to the fact that inductance typically only plays a role in the AC components of the system 48, while having no effect on the DC components. Thus, the capacitors may charge to a small DC voltage, e.g., similar to a half bridge configuration in which C carries a DC bus/2 voltage.

Additionally, in embodiments, the output leads of the modules may be substantially symmetrical such that their radiated emissions cancel each other.

Finally, it is also to be understood that the systems 10 and/or 48 may include the necessary electronics, software, memory, storage, databases, firmware, logic/state machines, microprocessors, communication links, displays or other visual or audio user interfaces, printing devices, and any other input/output interfaces to perform the functions described herein and/or to achieve the results described herein. For example, as previously mentioned, the system 10 and/or 48 may include at least one processor and system memory/data storage structures, which may include random access memory (RAM) and read-only memory (ROM). The at least one processor of the systems 10 and/or 48 may include one or more conventional microprocessors and one or more supplementary co-processors such as math co-processors or the like. The data storage structures discussed herein may include an appropriate combination of magnetic, optical and/or semiconductor memory, and may include, for example, RAM, ROM, flash drive, an optical disc such as a compact disc and/or a hard disk or drive.

Additionally, a software application that adapts the controller to perform the methods disclosed herein may be read into a main memory of the at least one processor from a computer-readable medium. The term "computer-readable medium," as used herein, refers to any medium that provides or participates in providing instructions to the at least one processor of the systems 10 and/or 48 (or any other processor of a device described herein) for execution. Such a medium may take many forms, including but not limited to, non-volatile media and volatile media. Non-volatile media include, for example, optical, magnetic, or opto-magnetic disks, such as memory. Volatile media include dynamic random access memory (DRAM), which typically constitutes the main memory. Common forms of computer-readable media include, for example, a floppy disk, a flexible disk, hard disk, magnetic tape, any other magnetic medium, a CD-ROM, DVD, any other optical medium, a RAM, a PROM, an EPROM or EEPROM (electronically erasable programmable read-only memory), a FLASH-EEPROM, any other memory chip or cartridge, or any other medium from which a computer can read.

While in embodiments, the execution of sequences of instructions in the software application causes at least one processor to perform the methods/processes described herein, hard-wired circuitry may be used in place of, or in combination with, software instructions for implementation of the methods/processes of the present invention. Therefore, embodiments of the present invention are not limited to any specific combination of hardware and/or software.

It is further to be understood that the above description is intended to be illustrative, and not restrictive. For example, the above-described embodiments (and/or aspects thereof) may be used in combination with each other. Additionally, many modifications may be made to adapt a particular situation or material to the teachings of the invention without departing from its scope.

For example, in an embodiment, a system for providing electrical power to a load is provided. The system includes at least two inverters and at least two resonant circuits. The inverters are operative to electrically connect to a power source. The resonant circuits are each electrically connected to at least one of the inverters and operative to provide electrical power to the load. The resonant circuits are coupled to each other. In certain embodiments, the resonant circuits are coupled to each other via one or more inductors disposed within the resonant circuits. In certain embodiments, each inverter is operative to connect to the power source via one or more input leads, and the resonant circuits are further coupled to each other via one or more inductors disposed in the input leads. In certain embodiments, the inverters and the resonant circuits are connected in series to the load. In certain embodiments, the inverters and the resonant circuits are connected in parallel to the load. In certain embodiments, each inverter is electrically connected to two of the resonant circuits. In certain embodiments, the inverters are operative to vary the electrical power provided to the load. In certain embodiments, the system further includes an electromagnetic radiation based imaging device having a radiation source. In such embodiments, the radiation source is the load.

Other embodiments provide for a method of providing electrical power to a load. The method includes providing electrical power to the load via one or more resonant circuits each electrically connected to at least one of two inverters electrically connected to a power source. The resonant circuits are coupled to each other. In certain embodiments, the resonant circuits are coupled to each other via one or more inductors disposed within the resonant circuits. In certain embodiments, each inverter is electrically connected to the power source via one or more input leads, and the resonant circuits are further coupled to each other via one or more inductors disposed in the input leads. In certain embodiments, the inverters and the resonant circuits are connected in series to the load. In certain embodiments, the inverters and the resonant circuits are connected in parallel to the load. In certain embodiments, each inverter is electrically connected to two of the resonant circuits. In certain embodiments, the method further includes varying the power provided to the load via the inverters.

Yet still other embodiments provide for a non-transitory computer readable medium storing instructions. The instructions are configured to adapt a controller to vary electrical power provided to a load by two resonant circuits that are each connected to at least one of two inverters electrically connected to a power source. The resonant circuits are coupled to each other. In certain embodiments, the stored instructions adapt the controller to vary the electrical power by adjusting the inverters. In certain embodiments, the controller adjusts the inverters by controlling one or more switches disposed within the inverters. In certain embodiments, the inverters are fully-bridged. In certain embodiments, the load is a radiation source of an electromagnetic radiation based imaging device.

As will be appreciated, by providing for the coupling of resonant circuits electrically connected to inverters, some embodiments of the present invention provide for resonant inverter modules that are stackable/chainable, in serial and/or parallel configurations, utilizing a common and substantially repeating wiring scheme such that n modules may result in n times the electrical power of an individual inverter/module. For example, some embodiments of the present invention may provide for an x-ray generator having four (4) inverters coupled to resonant circuits, e.g., 25 kW brick converters, that provide for one or more discrete power settings, e.g., 25 kW, 50 kW, 80 kW, and/or 100 kW. Thus, some embodiments of the present invention provide for improved designs and/or manufacturing of power supplies and convertors over traditional systems and methods thereof.

Further, by chaining together multiple modules, some embodiments provide for improved redundancy over traditional systems.

Additionally, while the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, terms such as "first," "second," "third," "upper," "lower," "bottom," "top," etc. are used merely as labels, and are not intended to impose numerical or positional requirements on their objects. Further, the limitations of the following claims are not written in means-plus-function format are not intended to be interpreted as such, unless and until such claim limitations expressly use the phrase "means for" followed by a statement of function void of further structure.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

Since certain changes may be made in the above-described invention, without departing from the spirit and scope of the invention herein involved, it is intended that all of the subject matter of the above description shown in the accompanying drawings shall be interpreted merely as examples illustrating the inventive concept herein and shall not be construed as limiting the invention.

What is claimed is:

1. A system for providing electrical power to a load comprising:
    at least two inverters operative to electrically connect to a power source;
    at least two resonant circuits that are each electrically connected to at least one of the inverters and operative to provide electrical power to the load;
    wherein the at least two resonant circuits are coupled to each other via a first inductance by a first inductor and a second inductance by a second inductor; and
    wherein the at least two resonant circuits are coupled to each other via the first and the second inductors disposed within the resonant circuits.

2. The system of claim 1, wherein each inverter is operative to connect to the power source via one or more input leads, and the at least two resonant circuits are further coupled to each other via one or more additional inductors disposed in the input leads.

3. The system of claim 1, wherein the at least two inverters and the at least two resonant circuits are connected in series to the load.

4. The system of claim 1, wherein the at least two inverters and the at least two resonant circuits are connected in parallel to the load.

5. The system of claim 1, wherein each inverter is electrically connected to two of the at least two resonant circuits.

6. The system of claim 1, wherein the at least two inverters are operative to vary the electrical power provided to the load.

7. The system of claim 1 further comprising an electromagnetic radiation based imaging device having a radiation source; and wherein the radiation source is the load.

8. A method of providing electrical power to a load comprising:
    providing electrical power to the load via one or more resonant circuits that are each electrically connected to at least one of two inverters that are electrically connected to a power source;
    wherein the resonant circuits are coupled to each other via a first inductance by a first inductor and a second inductance by a second inductor;
    wherein the resonant circuits are coupled to each other via the first and the second inductors disposed within the resonant circuits.

9. The method of claim 8, wherein each inverter is electrically connected to the power source via one or more input leads, and the resonant circuits are further coupled to each other via one or more additional inductors disposed in the input leads.

10. The method of claim 8, wherein the two inverters and the one or more resonant circuits are connected in series to the load.

11. The method of claim 8, wherein the two inverters and the one or more resonant circuits are connected in parallel to the load.

12. The method of claim 8, wherein each inverter is electrically connected to two of the one or more resonant circuits.

13. The method of claim 8 further comprising varying the power provided to the load via at least one of the two inverters.

14. A non-transitory computer readable medium storing instructions configured to adapt a controller to:
    vary electrical power provided to a load by a first resonant circuit and a second resonant circuit that are both connected to at least one of two inverters that are electrically connected to a power source, wherein the first and the second resonant circuits are coupled to each other via a first inductance by a first inductor and a second inductance by a second inductor disposed in the first and the second resonant circuits, respectively;
    wherein the controller adjusts at least ne of the two inverters by controller one or more switches disposed within the inverters.

15. The non-transitory computer readable medium of claim 14, wherein the stored instructions adapt the controller to vary the electrical power by adjusting at least one of the two inverters.

16. The non-transitory computer readable medium of claim 15, wherein the inverters are fully-bridged.

17. The non-transitory computer readable medium of claim 14, wherein the load is a radiation source of an electromagnetic radiation based imaging device.

* * * * *